(12) United States Patent
Tyagi et al.

(10) Patent No.: US 8,559,002 B2
(45) Date of Patent: Oct. 15, 2013

(54) METHOD FOR THE FORMATION OF SERS SUBSTRATES

(75) Inventors: Som Tyagi, Garnet Valley, PA (US); Kambiz Pourrezaei, Gladwyne, PA (US)

(73) Assignee: Drexel University, Philadelphia, PA (US)

( * ) Notice: Subject to any disclaimer, the term of this patent is extended or adjusted under 35 U.S.C. 154(b) by 200 days.

(21) Appl. No.: 12/933,001

(22) PCT Filed: Mar. 20, 2009

(86) PCT No.: PCT/US2009/037784
§ 371 (c)(1),
(2), (4) Date: Oct. 20, 2010

(87) PCT Pub. No.: WO2009/117646
PCT Pub. Date: Sep. 24, 2009

(65) Prior Publication Data
US 2011/0026019 A1    Feb. 3, 2011

Related U.S. Application Data

(60) Provisional application No. 61/038,217, filed on Mar. 20, 2008.

(51) Int. Cl.
| | | |
|---|---|---|
| *G01J 3/44* | (2006.01) | |
| *C23C 16/52* | (2006.01) | |
| *B05D 1/12* | (2006.01) | |
| *B05D 3/02* | (2006.01) | |

(52) U.S. Cl.
USPC ............. 356/301; 427/8; 427/180; 427/383.1

(58) Field of Classification Search
USPC .................. 356/301, 952; 101/487, 488; 427/541–543, 557, 379, 380, 180–206, 427/8
See application file for complete search history.

(56) References Cited

U.S. PATENT DOCUMENTS 4,802,761 A * 2/1989 Bowen et al. ................. 356/301
6,242,264 B1   6/2001 Natan (Continued)

FOREIGN PATENT DOCUMENTS

| WO | 02074899 A1 | 9/2002 |
|---|---|---|
| WO | 03083480 A1 | 9/2003 |

(Continued)

OTHER PUBLICATIONS

RG Freeman et al. "Ag-Clad Au Nanoparticles: Novel Aggregation, Optical, and Surface-Enhanced Raman Scattering Properties", J. Phys. Chem. 1996, 100, 718-724.*

(Continued)

*Primary Examiner* — Kara E Geisel
*Assistant Examiner* — Hina F Ayub
(74) *Attorney, Agent, or Firm* — Mendelsohn, Drucker & Dunleavy, P.C.

(57) ABSTRACT

A method for the formation of surface enhanced Raman scattering substrates. The method produces thin substrates that have a nanoparticle ink deposited thereon. The nanoparticle ink may be any suitable nanoparticle ink such as silver, gold or copper nanoparticle ink which includes stabilized nanoparticles. The substrates and nanoparticle ink undergo a first step of heating in order to remove liquid vehicle from the ink. The substrates and nanoparticles then undergo a second step of heating for an amount of time sufficient to remove a substantial portion of the stabilizer and provide a fractal aggregate nanoparticle layer on the substrate having a certain resistivity or conductivity suitable for Raman scattering. This creates SERS substrates with enhanced amplification properties.

14 Claims, 16 Drawing Sheets

(56) References Cited

U.S. PATENT DOCUMENTS

| | | |
|---|---|---|
| 6,514,767 B1 | 2/2003 | Natan |
| 6,989,897 B2 | 1/2006 | Chan |
| 7,108,915 B2 | 9/2006 | Adams |
| 7,192,778 B2 | 3/2007 | Natan |
| 7,361,410 B2 | 4/2008 | Zhang |
| 7,397,558 B2 | 7/2008 | Kamins |
| 7,400,395 B2 | 7/2008 | Chan |
| 7,427,526 B2 | 9/2008 | Fonash |
| 7,443,027 B2 | 10/2008 | Wu |
| 7,443,789 B2 | 10/2008 | Glaser |
| 8,206,616 B2 * | 6/2012 | Yu et al. .................. 252/519.3 |
| 2002/0020053 A1 | 2/2002 | Fonash |
| 2003/0029274 A1 | 2/2003 | Natan |
| 2003/0157732 A1 * | 8/2003 | Baker et al. ............... 436/531 |
| 2004/0038264 A1 | 2/2004 | Souza |
| 2004/0096981 A1 | 5/2004 | Weimer |
| 2006/0060885 A1 | 3/2006 | Wu |
| 2006/0141268 A1 | 6/2006 | Kalkan |
| 2007/0165209 A1 | 7/2007 | Natan |
| 2007/0285657 A1 | 12/2007 | Wang |
| 2010/0075137 A1 * | 3/2010 | Sinton et al. ............... 428/328 |

FOREIGN PATENT DOCUMENTS

| | | |
|---|---|---|
| WO | 2006060734 A2 | 6/2006 |
| WO | 2006065762 A2 | 6/2006 |

OTHER PUBLICATIONS

DW Schaefer et al. "Fractal Geometry of Colloidal Aggregates", Phys. Rev. Letters 1984, (52) 26, 2371-2375.*

Solomon, et al., "Synthesis and Study of Silver Nanoparticles," Journal of Chemical Education, Feb. 2007, pp. 322-325, vol. 84, No. 2, Philadelphia, Pennsylvania.

V.M. Shalaev, Nonlinear Optics of Random Media: Fractal Composites and Metal-Dielectric Films, Springer, Heidelberg (2000).

Jean-Francois Gouyet, Physics and Fractal Structure, Springer, Berlin, 1996, Chapter 1.

Podolskiy, Giant Optical Responses in Microactivity-Fractal Composites, Laser Physics, Jul. 16, 2000, pp. 26-30, vol. 11, No. 1, Las Cruces, New Mexico.

M. A. Figueroa, S. Park, K. Pourrezaei, and S. Tyagi, "Development of surface-enhanced Raman scattering (SERS) substrates" Proc. SPIE vol. 6866, 668610-1-5 (2008).

Manuel Figueroa, William Stephenson, Kambiz Pourrezaei, Somdev Tyagi, "Characterization of surface enhanced Raman scattering (SERS) substrates fabricated from colloidal printing inks," Proc. of SPIE vol. 7576, 75761T (2010).

* cited by examiner

METHOD FOR THE FORMATION OF SERS SUBSTRATES

RELATED APPLICATION DATA

This application is a non-provisional of U.S. Provisional application No. 61/038,217 filed Mar. 20, 2008, the contents of which are hereby incorporated by reference.

FUNDING ACKNOWLEDGEMENT

Some research for this invention was supported by the Commonwealth of Pennsylvania's Ben Franklin Technology Development Authority through the Ben Franklin Technology Partners of Southeastern Pennsylvania as fiscal agents for the Nanotechnology Institute.

BACKGROUND OF THE INVENTION

1. Field of the Invention

The present invention is directed to a method for forming surface-enhanced Raman scattering (SERS) substrates. In particular, it is directed to a method for forming SERS substrates using nanoparticle-based films.

2. Description of the Related Technology

Raman scattering spectroscopy (RSS) is the measurement of the wavelength and intensity of light scattered inelastically from a molecule. Raman scattering is the result of an inelastic collision of a photon with atoms. Both elastic and inelastic collisions occur when light interacts with a molecule. In elastic collisions (Rayleigh scattering), an atom is excited from a ground state to a higher energy state and then relaxes back to the original ground state, thereby emitting a photon at the same frequency as the incident light. However in an inelastic collision, the excited molecule relaxes to a different vibrational state rather than the original state, thereby scattering energy different from that of the incident light. If the scattered energy is higher than the incident light it is called an Anti-Stokes line (blue shifted), if it is lower it is called a Stokes line (red shifted).

FIG. 1 represents a schematic of the Raman spectrum. RS gives information about the characteristic vibrational states of the chemical bonds of molecules. It is a widely used spectroscopic tool for the determination of molecular structure and for compound identification. Despite all these advantages, its use has been somewhat limited due to its poor efficiency. RSS when compared to fluorescence spectroscopy has a small Scattering Cross Section ($10^{-30}$ cm$^2$ per molecule when compared to $10^{-16}$ cm$^2$ for fluorescence) thus reducing the possibility of analyzing compounds of biological significance due to the generally low concentration of analytes in biological samples of this size.

However, due to the availability of better SERS substrates in the past decade, the SERS technique has seen a remarkable surge in its use, especially for the detection of biologically significant molecules such as toxins and disease-related molecules.

There is a way to greatly enhance the Raman signal by using specially structured metallic substrates, typically constructed of Ag, Au, and Cu. Such Surface Enhanced Raman Scattering was first reported in 1974 where a large enhancement of Raman signals of pyridine molecules adsorbed on electrochemically roughened silver electrodes was observed. SERS amplification factors of between $10^6$~$10^{16}$ have been achieved using a wide range of SERS substrates. This enhancement effect has made RS an increasingly important analytical tool in biological sciences. It must be mentioned though that despite numerous physical models that have been proposed to explain SERS, it is generally agreed that a complete theoretical understanding of the SERS mechanisms remains elusive.

There is a serious drawback that plagues all SERS substrates and makes them less than promising candidates for SERS imaging. Typical SERS substrates are fabricated by methods that result in the noble metal nanostructures stochastically distributed over the substrate surface, e.g. electrochemically roughened electrodes, sputtered films, chemically etched films, electroless deposited films, and colloidal metal particles. Another way to obtain large amplification in Raman scattering is to place the sample in close proximity to a sharp metallic tip. This stochastic nature leads to randomly distributed Raman "hot spots" and results in a lack of reproducibility in most SERS substrates. It is therefore desirable to create a substrate that can induce enhanced Raman scattering homogeneously over the entire sample area in order to provide enhanced Raman imaging.

By using controlled patterning of the nanostructures with electron-beam and other lithographic techniques, little randomness remains and one can expect SERS to be homogeneous across the proposed substrate. Such substrates are now commercially available (Mesophotonics Limited, Southampton, UK). Fabrication of such substrates involves a multi-step process and the resulting substrates are quite expensive. Such substrates are also small in size, for example, between 4 mm×4 mm.

An advantage of RS is that it offers, without the need for labeling, molecular-level specificity at sub-micron spatial resolutions. While a number of other imaging techniques employing confocal microscopes also offer molecular-level specificity at sub-micron resolutions, all of them require certain forms of labeling on the sample. These various labeling techniques, e.g. Green Fluorescence Protein, immuno-labeling, staining, fluorescence, luminescence, etc, inevitably alter the very sample under examination as they achieve the specificity critical for bio-imaging.

RS, on the other hand, probes the inherent vibrational states of a molecule and therefore attains chemical specificity without the need for labeling. However, the Raman scattering signals from those vibrational states are relatively weak. In order to obtain a satisfactory signal-to-noise ratio, one has to either increase the intensity of the probing laser or resort to surface enhanced Raman scattering. For biological applications, increased laser intensity often limits the in vivo imaging capability of a system. It is therefore desirable to create SERS structures that permit the ability to use enhanced bio-imaging.

One of the most common methods to enhance the Raman signal is by using colloidal silver or gold nanoparticles. The largest SERS signal amplification is achieved when the analyte molecule is sandwiched between two nanoparticles and when the polarization vector, i.e. the direction of the oscillating E-field of the laser's electromagnetic field, is along the line connecting the centers of the Ag nanoparticles. Amplification factors in the range of $6*10^6$ to $2.5*10^{10}$ have been predicted when the separation between two Ag nanoparticles of diameter 90 nm is varied between 5.5 and 1.0 nm. When the polarization vector is perpendicular to the Ag nanoparticles, the maximum amplification factor is relatively small (about 1 to 10). In FIG. 2 the polarization vector with respect to the molecules is shown The amplification factor for the geometry indicated in [c] is intermediate between cases [a] and [b] See e.g. H. Xu, et al. "Spectroscopy of single Hemoglobin molecules by surface enhanced Raman scattering," *Phys. Rev. Lett.* 83, 43574360 (1999).

To produce such favorable geometries as depicted in FIG. 2, and in other compact aggregates, the analyte is incubated in an Ag colloidal suspension (in water or other suitable liquid organic carrier) with 1.0-10.0 mM NaCl solution. The role of NaCl is as an aggregating agent. The Ag aggregates are then sorted according to their size and compact aggregates (two to about ten particles each) and isolated for further study using SERS. There are two drawbacks to this technique of creating compact Ag aggregates. First, there is poor control over the size of the aggregates produced. The creation of hot spots for Raman scattering largely results as accidental byproducts of the technique. Second, the yield of the desired aggregates is very low and the suitable portions of the nanoparticle array on the substrate must then be selected from a mixture of larger aggregates before they can be used for SERS study. This prevents the fabrication of suitable SERS substrates on a large scale.

U.S. Pat. No. 6,989,897 B2 provides metal-coated nanocrystalline silicon as an active surface-enhanced Raman scattering substrate. This patent provides the required spacing between active nanoparticles by patterning the substrate to receive the nanoparticles at desired locations and then locating the nanoparticles in the patterned locations on the substrate.

U.S. Pat. No. 6,242,264 provides a dip coating method for coating nanoparticles onto a surface of a glass slide for use in Raman scattering. In the process, the glass slide is dipped first coated with an adhesion promoting material and then dipped into a solution containing the nanoparticles for a time period sufficient to provide the required density of nanoparticles on the surface of the glass slide. This method does not appear to provide fractal aggregates of the nanoparticles but instead generates concentration gradients along the slide due to the use of the dip coating method. Further, dip coating is limited in its commercial applicability.

U.S. patent application publication No. 2006/0060885 discloses a method for depositing a conductive nanoparticle layer onto a substrate surface. A solution of stabilized nanoparticles is applied to a substrate surface and heated to remove liquid vehicle and stabilizer until a nanoparticle layer is formed. Heating is continued until a minimum conductivity of 1 Siemens/centimeter is achieved in order to provide the conductive coating.

A fractal is a self-similar geometrical object—it looks the same at any length scale. In practice this self similarity does not extend infinitely due to the finite sample size. Jean-Francois Gouyet, *Physics and Fractal Structure*, Springer, Berlin, 1996, Chapter 1.

Metallic fractal aggregates can exhibit some of the highest SERS signal amplification factors. V. M. Shalaev, *Nonlinear Optics of Random Media. Fractal Composites and Metal-Dielectric Films*, Springer, Heidelberg (2000). Ideally, a fractal has the property that it looks the same at any scale. In practice this structural scale invariance will be limited by finite sample size.

Fractal aggregates of metallic colloidal particles can provide enhancement for various linear and nonlinear optical responses, including Raman scattering. The basic mechanism that gives rise to such enhancement arises from the localization of optical plasmon excitations within small parts ("hot-spots") of a fractal aggregate. Such "hot spots", are usually much smaller (tens of nm) than the size of the fractal and often much smaller than the wavelength. Fractal structures, unlike translationally invariant media, cannot support propagating waves and hence can confine electromagnetic field to very small regions of the substrate. If sufficiently concentrated, the enhanced electromagnetic fields in the hot spots can result in SERS signal amplification. The small areas, where the fractal optical excitations are localized, have very different local structures and, therefore, are characterized by different resonant frequencies.

The various nano-scale regions, where the resonant fractal excitations are localized, act as a collection of different optical "nano-resonators", resulting in a distribution of resonance frequencies in the visible and IR spectral ranges and can have resonance quality-factors as large as $10^3$. When Stokes shifts are small, the SERS signal is roughly proportional to the local field raised to the fourth power and, therefore, it can be enhanced up to $10^{12}$ in the fractal hot spots. Such amplification factors can be further enhanced by chemical enhancement. See V. M. Shalaev, *Nonlinear Optics of Random Media: Fractal Composites and Metal-Dielectric Films*, Springer, Heidelberg (2000).

Therefore, there is a need in the field to provide a method for forming SERS substrates in manner that permits control of the average distance between nanoparticles and to be able to produce SERS substrates in larger numbers at lower cost.

SUMMARY OF THE INVENTION

An object of the invention is a method for producing SERS substrates that have enhanced amplification.

Yet another object of the invention is a method for controlling the average distance between nanoparticles on an SERS substrate.

An aspect of the invention may be a method for fabricating SERS substrates comprising: providing a substrate; applying a nanoparticle ink to a surface of the substrate, wherein the nanoparticle ink comprises a liquid and a plurality of nanoparticles; heating the nanoparticle ink and the substrate for a period of time, whereby a surface enhanced Raman scattering substrate is formed.

Yet another aspect of the invention can be a SERS substrate comprising: a substrate and a fractal aggregate of a plurality of nanoparticles attached to the substrate.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Currently there are no commercially available SERS substrates that use colloids in the production process. Most researchers make their own substrates on an as-needed basis. SERS substrates made by a lithographic process have two limitations, first, they are very expensive to produce since one needs sophisticated and expensive infrastructure in order to perform the process; and second, even if the cost of producing them is brought down the size of the largest SERS substrate will be limited by the wafer size on which the nanostructures are inscribed.

Figure 1:
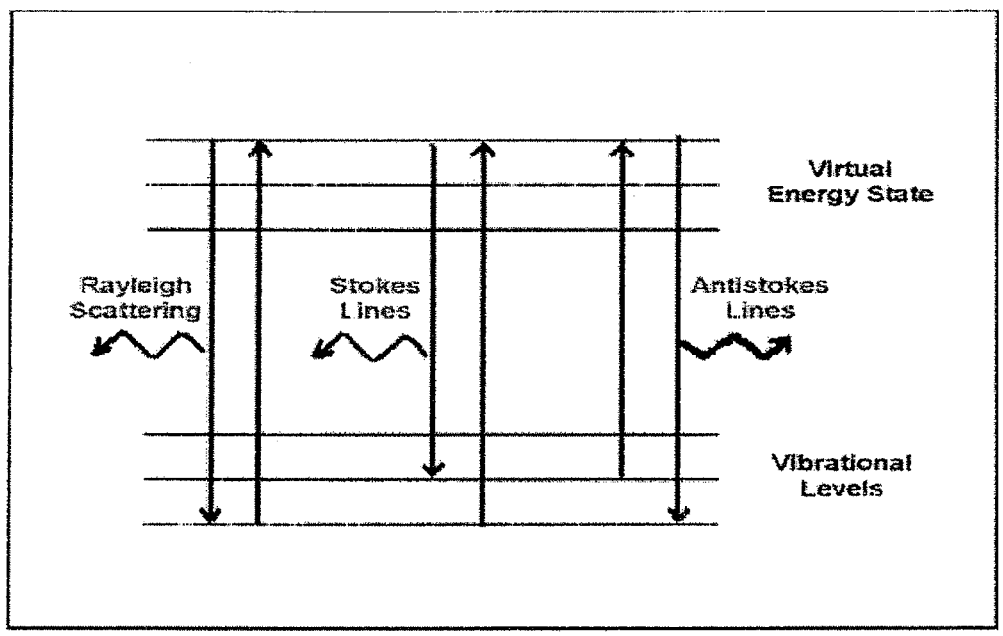
FIG. 1 is a diagram illustrating the types of Raman scattering.
Figure 2:
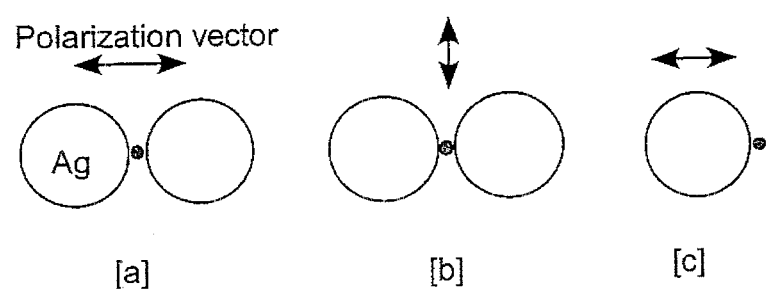
FIG. 2 shows the polarization vector with respect to molecules.
Figure 3A:
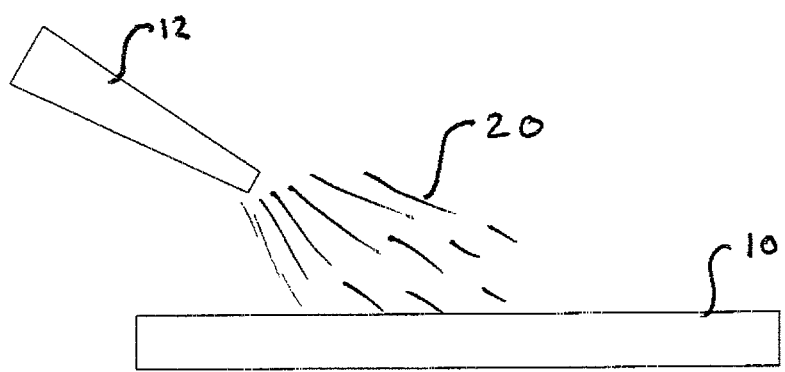
FIG. 3(a) is a diagram of an applicator and a substrate in accordance with an embodiment of the present invention.
Figure 3B:
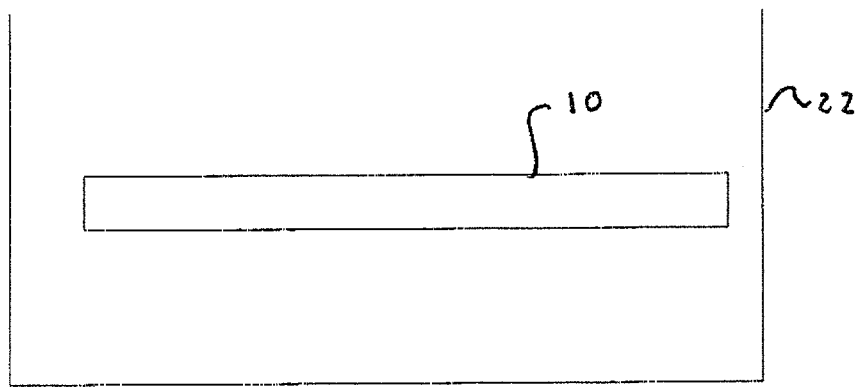
FIG. 3(b) is a diagram of a substrate and an oven in accordance with an embodiment of the present invention.

The method of the present invention can be used to produce SERS substrates inexpensively and can be scaled up to produce, for example, meters per minute of a 10.0 cm wide SERS substrate. A diagram illustrating the system for the formation of a SERS substrate is shown in FIGS. 3(a) and 3(b). The steps for forming a SERS substrate are shown in FIG. 4.

In FIG. 3(a) a diagram illustrating the application of nanoparticle ink 20 onto a substrate 10 is shown. The nanoparticle ink 20 may be applied in a variety of ways, and is schematically represented as being applied via applicator 12 shown in FIG. 3(a). Nanoparticle ink 20 may be applied via airbrushing, ink jet printing, silk screen printing, stamping, gravure printing methods and/or flexographic printing. It should be understood that the method for applying nanoparticle ink 20 to substrate 10 is not limited to any one method and may include any method that will form a suitable thin film on substrate 10. Suitable substrates 10 may include, but are not limited to, glass, quartz, polyester, polyethylene, liquid crystal polymer (LCP), polypropylene, silicon, polyimide, etc. Substrates 10 can be used with or without being coated with adhesion-promoting materials. Suitable substrates include, but are not limited to, inflexible inorganic substrates such as glass or flexible organic substrates such as polyimide or polyethylene. In some implementations, paper substrates can be used. Other substrates may be used as well.

FIG. 3(b) is a diagram of a substrate 10 and an oven 22. During the heating steps, substrate 10 may be placed into the oven 22 and heated to the desired temperature(s). In some embodiments more than one oven 22 may be used. Heating may also be achieved by such means as microwaves and laser heating.

Figure 4:
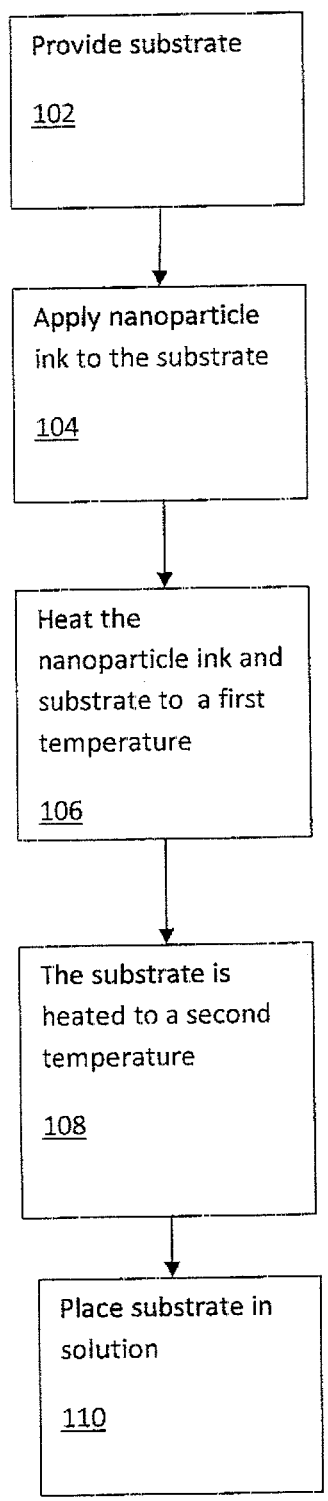
FIG. 4 is flow chart of a method for forming the SERS substrate in accordance with an embodiment of the present invention.

Now referring to FIGS. 4 and 5(a)-5(c), wherein the process for forming the SERS substrate and the materials used in the process are shown. In FIG. 4, a flow chart illustrating the steps used in forming a SERS substrate is shown. In step 102 one or more substrates 10 are provided. In step 104, the nanoparticle ink 20 is applied to one or more substrates 10.

In the embodiment discussed herein, a silver (Ag) nanoparticle ink 20 is used. Nanoparticle ink 20 may have nanoparticles 18 that are between 15-50 nm in diameter and comprise up to 1% by weight of the total weight of the nanoparticle ink located within a liquid vehicle 15. However it should be understood that the process is not limited to the use of silver nanoparticle ink 20, but can be applied to other conductive nanoparticle inks 20, such as Au and Cu. The nanoparticle ink 20 also includes a liquid vehicle 15 which may optionally include an adhesion promoter, surfactants and/or rheology modifiers; and a stabilizer 17, which acts as an agglomeration preventer and/or rheology modifier.

A suitable liquid vehicle 15 for the nanoparticle ink may be selected from, for example, water, ketones, alcohols, esters, ethers, halogenated aliphatic and aromatic hydrocarbons and the like and mixtures thereof. Specific examples of suitable liquid vehicles are cyclohexanone, acetone, methyl ethyl ketone, methanol, ethanol, butanol, amyl alcohol, butyl acetate, dibutyl ether, tetrahydrofuran, toluene, xylene, chlorobenzene, methylene chloride, trichloroethylene, and the like. A single material or a mixture of two, three or more different materials from the foregoing list can be used in any combination and at any suitable ratio such as an equal or unequal ratio of two or more different fluids.

Adhesion promoters may be materials such as polytetrafluoroethylene and metal complexes of Pd, Mg, W, Ni, Cr, Bi, B, Sn, In, Pt. The adhesion promoters permit the nanoparticles 18 to remain attached to the surface of the substrate 10, after the heating process.

The stabilizer 17 may be any moiety that "stabilizes" the nanoparticles 18 prior to and/or during deposition of the nanoparticle ink 20, where "stabilizes" refers to reducing the aggregation and precipitation of the nanoparticles 18. Preferred stabilizers 17 are those that "stabilize" metal nanoparticles 18 at room temperature, which refers herein to a temperature of about 20° C. to about 28° C., or any other desired temperature range. The stabilizer 17 may be a single stabilizer 17 or a mixture of two or more stabilizers 17. In some embodiments, the stabilizer 17 may have a boiling point or decomposition temperature lower than about 250° C., particularly lower than about 150° C., under 1 atmosphere or reduced pressure for example from several mbar to about $10^{-3}$ mbar.

The stabilizer 17 may be a coating or partial coating which may be made of a material such as PVP (polyvinylpyrrolidone), another polymer, or borohydride. Polymers that have been successfully used in the formulation of inks are Triton X-100, Triton X-15, Triton X-45, Triton QS-15, linear alkyl ether (colar Cap MA259, colar Cap MA1610), quaternized alkyl imidazoline (Cola Solv IES and Cola Solv TES), polyvinyl alcohol, polyethylene glycol, and polysiloxanes. The weight percentage of stabilizers may vary from 0.5% to 20%. The loading concentration of nanoparticles may be from 10% to up 60%.

The rationale behind the use of polymers as stabilizers 17 is that they often have higher viscosities than do the typical liquids used as vehicles in conductive inks, and that because of their multiple binding sites to metal nanoparticles, they can be used in lower concentrations than monomeric dispersants, and still confer monolayer coverage of the metal nanoparticle. Higher viscosities are important because they facilitate the creation of good dispersions and inks that can be printed using inkjet methods. Lower concentrations of the dispersant are favorable because there is less organic material to be removed during the curing process.

In some embodiments, the stabilizer 17 may be an organic stabilizer. The term "organic" in "organic stabilizer" refers to the presence of carbon atom(s), but the organic stabilizer may include one or more non-metal heteroatoms such as nitrogen, oxygen, sulfur, silicon, a halogen, and the like. Exemplary organic stabilizers include for instance thiol and its derivatives, amine and its derivatives, carboxylic acid and its carboxylate derivatives, polyethylene glycols, and other organic surfactants. In some embodiments, the organic stabilizer is selected from the group consisting of a dithiol such as for example 1,2-ethanedithiol, 1,3-propanedithiol, and 1,4-butanedithiol; a diamine such as for example ethylenediamine, 1,3-diaminopropane, 1,4-diaminobutane; a thiol such as for example 1-butanethiol, 1-pentanethiol, 1-hexanethiol, 1-heptanethiol, 1-octanethiol, 1-dodecanethiol, and tert-dodecanethiol; an amine such as for example 1-ethylamine, 1-propylamine, 1-butylamine, octylamine and dodecylamine; a mixture of a thiol and a dithiol; and a mixture of an amine and a diamine, particularly a low boiling point version of any of the above. Organic stabilizers containing a pyridine derivative (e.g., dodecyl pyridine) and/or organophosphine that can stabilize metal nanoparticles are also included as a stabilizer in embodiments of the present invention. In some embodiments, the metal nanoparticles 18 may form a chemical bond with the stabilizer 17. The chemical names of the stabilizer 17 provided herein are before formation of any chemical bond with the nanoparticles 18.

In some embodiments, the stabilizer 17 may be a metal containing stabilizer such as organometallic compounds or metal salts of organic compounds. Illustrative examples are metal alkoxides, metal carboxylates, alkyl ammonium salts of metal, and other metal containing compounds such as a metal alkylsulfonate or arylsulfonate, and a pyridinium salt of metal, or mixtures thereof. The metal of the metal containing stabilizer can be for example sodium, potassium, and calcium. In some embodiments of the present invention, the metal containing stabilizer is other than a metal-chelate complex. In embodiments of the present invention, the stabilizer is other than a metal containing stabilizer.

The extent of coverage of the stabilizer 17 on the surface of the nanoparticles 18 can vary for example from partial to full coverage depending for instance on the capability of the stabilizer 17 to stabilize the nanoparticles 18. Of course, there may also be variability in the extent of coverage of the stabilizer 17 among the individual nanoparticles 18. Stabilizer 17 may function as a barrier layer which prevents contact between surfaces of adjacent nanoparticles 18 and maintains a minimum spacing between nanoparticles 18 of about twice the coating thickness. Alternatively, stabilizer 17 may be in the form of a plurality of, for example, ligands bound to the surface of the nanoparticles which provide spacing between adjacent nanoparticles 18 via steric hindrance. Suitable stabilizers 17 must be capable of being partially or completely removed by heating the substrate 10 and nanoparticles at a temperature below which damage to the substrate 10 or nanoparticles 18 would occur.

Exemplary amounts of the composition components are as follows. The metal nanoparticles and the stabilizer may be present in an amount ranging for example from about 0.3% to about 90% by weight, or from about 1% to about 70% by weight, the balance being the other components of the composition such as the liquid vehicle. If the metal nanoparticles and the stabilizer(s) are added separately into the liquid vehicle, the metal nanoparticles are present in an amount ranging for example from about 0.1% to 90% by weight, or from about 1% to 70% by weight of the composition; the stabilizer or stabilizers are present in a sufficient amount to form a stable composition, for example in a range from about 1% to 50% by weight, or from about 5% to 40% by weight of the composition.

In step 104, the nanoparticle ink 20 is placed on the substrate 10. The nanoparticle ink 20 may be air-brushed onto the heated quartz substrate 10. Alternatively, Ag colloid films (made from inks that are 25-40% by weight Ag) can be deposited on polyimide substrates. Other processes for placing the ink 20 on the substrate 10 include, for example, solution printing techniques such as screen printing, stencil printing, inkjet printing, stamping (such as microcontact printing), and the like. The deposited ink 20 may have a thickness ranging from about 5 nm to about 1 millimeter, particularly from about 10 nm to 1 micrometer.

Still referring to FIG. 4, in step 106 the substrate 10 and the nanoparticle ink 20 may be heated to a suitable temperature for liquid vehicle removal, preferably, between about 60-120° C., more preferably, between about 80-100° C. in the oven 22. The period of time may be sufficient for liquid vehicle removal, for example, typically between 0-10 minutes. Heating to this temperature removes the liquid vehicle of the nanoparticle ink 20. The first heating step may also be sufficient to remove all or a portion of one or more of the other additives that may be present in the nanoparticles ink 20, such as the adhesion promoters, rheology modifiers, surfactants and some or all of the stabilizer 17, depending upon the particular ingredients employed in the ink.

In step 108, at least a portion of stabilizer 17 is controllably removed by heating. It should be understood, that the second heating step 108 may be a continuation of the first heating step 106 at a substantially higher temperature. Specifically, it is desirable to remove the liquid vehicle prior to removal of all or part of the stabilizer 17 to avoid large gaps that might otherwise be created by fast removal of the liquid vehicle. The length and duration of heating controls the removal of the stabilizer 17 which in turn affects the distance between the nanoparticles 18.

In performing step 108, substrate 10, which has deposited thereon nanoparticles 18 having the stabilizer 17 is heated to a suitable temperature to at least partially remove the stabilizer 17, for example, a temperature between about 100-250° C., more preferably, between about 150-200° C. for a period of time. The period of time may be sufficient to provide the desired end product, for example, a suitable time period may be about 1-30 minutes. As the stabilizer 17 is removed, the nanoparticles 18 may move closer to one another and a layer of nanoparticles 18 is formed on substrate 10.

The layer of nanoparticles 18 is not a continuous layer, but rather preferably includes a number of spaces 19, as shown in the figures. The heat treatment step 108, i.e. the temperature and the time for which the coated substrates are heated, can be adjusted to control the average distance between nanoparticles 18. The average distance between nanoparticles 18 is typically defined over the cross-sectional area of the laser beam used in the Raman scattering and thus references to "average distance" refer to an average distance determined over the cross-sectional area of a particular, predetermined laser beam suitable for use in Raman scattering.

The second heating step 108 is employed to remove a substantial portion of the stabilizer 17 that remains after the first heating step 106. It should be understood that the creation of nanoparticles or nanoparticle clusters located in close proximity to one another with a distribution of different spacing 19, is desired. Heating may cause separation of the stabilizer and the liquid from the metal nanoparticles in the sense that the stabilizer and the liquid are generally not incorporated into the formed nanoparticle layer but if present are in a residual amount. In embodiments, heating may decompose a portion of the stabilizer to produce "decomposed stabilizer."

Heating may also cause separation of the decomposed stabilizer such that the decomposed stabilizer generally is not incorporated into the nanoparticle layer, but if present is in a residual amount. Separation of the stabilizer, the liquid, and the decomposed stabilizer from the metal nanoparticles may lead to enhanced activity of the nanoparticle layer. Separation may occur in any manner such as for example a change in state of matter from a solid or liquid to a gas, e.g., volatilization. Separation may also occur when any one or more of the stabilizer, decomposed stabilizer, and liquid migrates to an adjacent layer and/or forms an interlayer between the nanoparticle layer and the adjacent layer, where intermixing of various materials optionally occurs in the adjacent layer and/or the interlayer.

In embodiments, one or more of the stabilizer, decomposed stabilizer, and the liquid is absent from the nanoparticle layer. In embodiments, a residual amount of one or more of the stabilizer, decomposed stabilizer, and the liquid may be present in the nanoparticle layer, where the residual amount does not appreciably affect the Raman scattering of the nanoparticle layer. In embodiments, the residual amount of one or more of the stabilizer, decomposed stabilizer, and the liquid may alter the Raman scattering of the nanoparticle layer but the resulting Raman scattering is still within the useful range for the intended device. The residual amount of each component may independently range for example of up to about 5% by weight, or less than about 0.5% by weight based on the weight of the nanoparticle layer, depending on the process conditions such as heating temperature and time. When heating causes separation of the stabilizer and/or decomposed stabilizer from the metal nanoparticles, the attractive force between the separated stabilizer/decomposed stabilizer and the metal nanoparticles is severed or diminished. Other techniques such as exposure to UV light may be combined with heating to accelerate the separation of the stabilizer, the liquid, and the decomposed stabilizer from the metal nanoparticles.

Step 110 is an optional step may be performed in order to remove any oxides that may have formed during steps 106 and 108. Step 110 involves placing the completed SERS substrates into a solution of acid, such as acetic acid or nitric acid. The acid facilitates removal of any oxides formed during the heating process.

The process described above with respect to FIG. 4 creates SERS substrates with enhanced amplification capabilities. The method of the invention forms fractal aggregates of nanoparticles on the substrate. The formation of fractal aggregates is particularly advantageous since it permits the SERS substrate to be used with a variety of different laser wavelengths since the SERS substrate will include Raman scattering "hot-spots" suitable for different laser wavelengths.

Figure 5A:
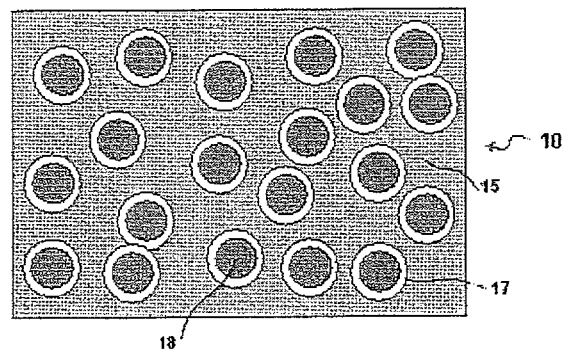
FIGS. 5(a)-5(c) schematically illustrate the effects of heat treatment on the nanoparticle ink.
Figure 5B:
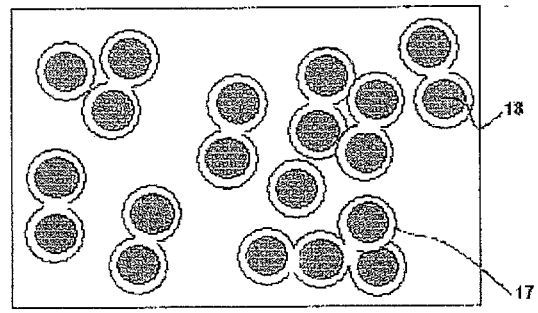
Figure 5C:
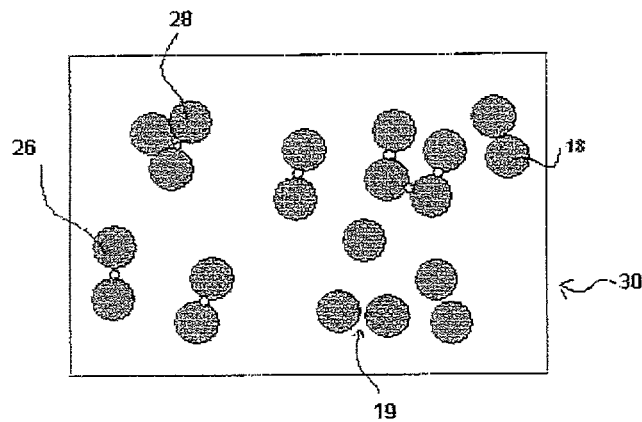

The heat treatment process of steps 106-108 discussed above with respect to FIG. 4 is schematically depicted in FIGS. 5(a)-5(c). FIG. 5(a) shows the components of the nanoparticle ink 20 when it is placed on the substrate 10. Shown are nanoparticles 18, liquid vehicle 15 and the stabilizer 17. FIG. 5(b) shows the substrate surface after removal of liquid vehicle 15 due to the first step of heating, step 106.

FIG. 5(c) shows the substrate surface after removal of stabilizer 17. The second step of heating may form the preferred arrangement of nanoparticles 18 that results in the fractal aggregates. In a fractal aggregate the distances between different sets of particles 18 form a range. The width of this distribution can be controlled by varying the time of the second heating step 108. As shown in FIG. 5(c), some of the resultant materials are spaced apart as indicated by 19, while some of the particles may be touching or bound or held together to form larger agglomerated particles 26 and 28.

One way to characterize a fractal is to determine the fractal dimension of the colloidal aggregate. There are various ways to determine the fractal dimension. For the purposes of the present application, the relationship between the area occupied by a cluster and its perimeter has been employed. The slope of the log-log plot is then used to determine the fractal dimension. This method is detailed in, for example, Jean-Francois Gouyet, *Physics and Fractal Structure*, Springer, Berlin, 1996, Chapter 3.

Figure 6A:
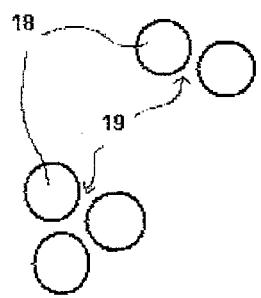
FIGS. 6(a)-6(c) show the potential arrangements of various nanoparticles during the formation of the SERS substrate.
Figure 6B:
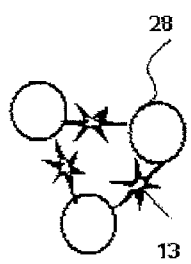
Figure 6C:
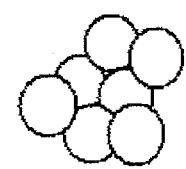

FIGS. 6(a)-6(c) show the potential arrangements of various nanoparticles 18 during the formation of the SERS substrate 30. In the process, at least two nanoparticles 18 are brought into proximity with each other, i.e. a minimum distance between the nanoparticles 18 is maintained. In order to obtain the fractal aggregate, a significant number of the nanoparticles 18 or nanoparticle clusters remain spaced apart from each other by a minimum distance of the order of a few nanometers, such as shown in FIG. 6(a) and the minimum distance between pairs of nanoparticles 18 or nanoparticle clusters varies from location to location. In other words, the nanoparticles 18 do not touch or sinter forming a bond 13, such as shown in FIG. 6(b). The spacing 19 between nanoparticles or nanoparticle agglomerates provides the SERS amplification and foul's "hot-spots." Fractal aggregation of the nanoparticles forms a nanoparticle layer having particles spaced at different distances from one another in a fractal distribution to thereby provide a variety of "hot-spots" suitable for different lasers in the same SERS substrate. This allows a single substrate to be used with a variety of different lasers, eliminating the need to customize SERS substrates for particular lasers. The number of spaces between particles that may exist on a SERs Substrate 30 will be diminished as an increasing number of interconnected clusters such as those shown in FIG. 6(c) are formed.

Figure 7:
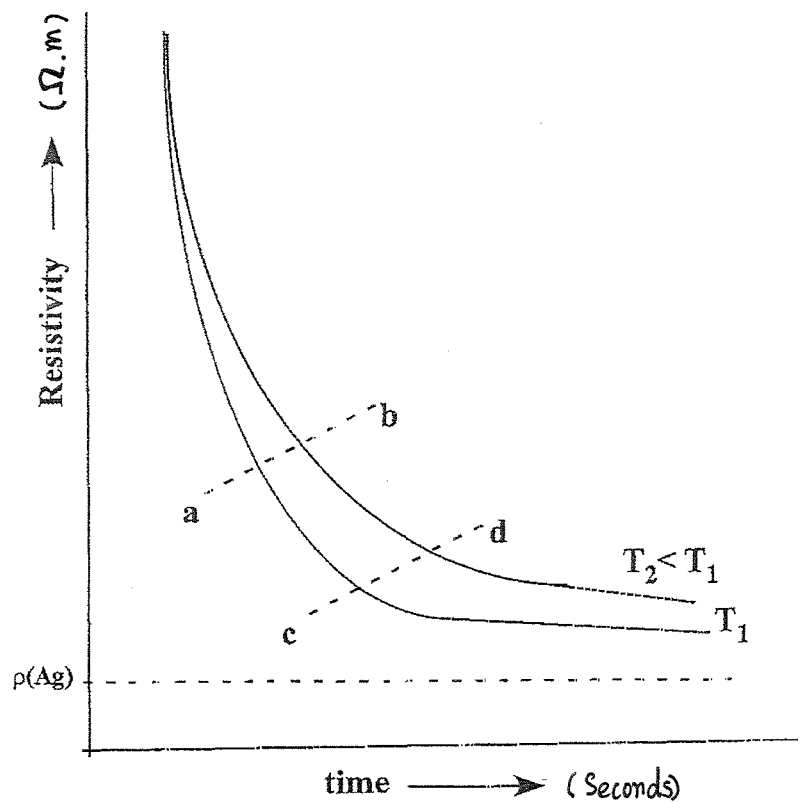
FIG. 7 is a graph illustrating a schematic plot of resistivity vs. time (t).

FIG. 7 is a graph illustrating a schematic plot of resistivity vs. time (t) as a function of time of heating (annealing) at two different temperatures $T_1$ and $T_2$ for silver colloidal films. Typically the annealing temperatures are in the range of 80-150° C. for the silver colloidal films. At t=0 these films have such high resistance that they are close to being electrical insulators for direct current conduction. This is due to the substantially complete isolation of nanoparticles 18 from each other. As the stabilizer 17 is removed, the nanoparticles 18 begin to move closer together and, in some cases, make isolated connections and the resistivity shows a decline. With prolonged time of annealing, typically 5 to 30 seconds (with shorter times at higher annealing temperatures) the resistivity can be lowered to within an order of magnitude of bulk silver which is $1.62*10^{-8}$ Ω.m (1.62 µΩ.cm). Typically, suitable SERS substrates have a conductivity of from about 2000 to about 5000 S/cm or a resistivity of from about 2.0 to $5.0*10^{-4}$ Ω-cm. The desired resisitivity for the SERS substrate 30 is a resistivity that corresponds to the situation where the nanoparticles 18 are not densely networked but are also not completely electrically isolated from each other. This happens in a region bound by, for example, the lines ab and cd of FIG. 7. This region can be monitored using the well-known four-point probe method.

Figure 8:
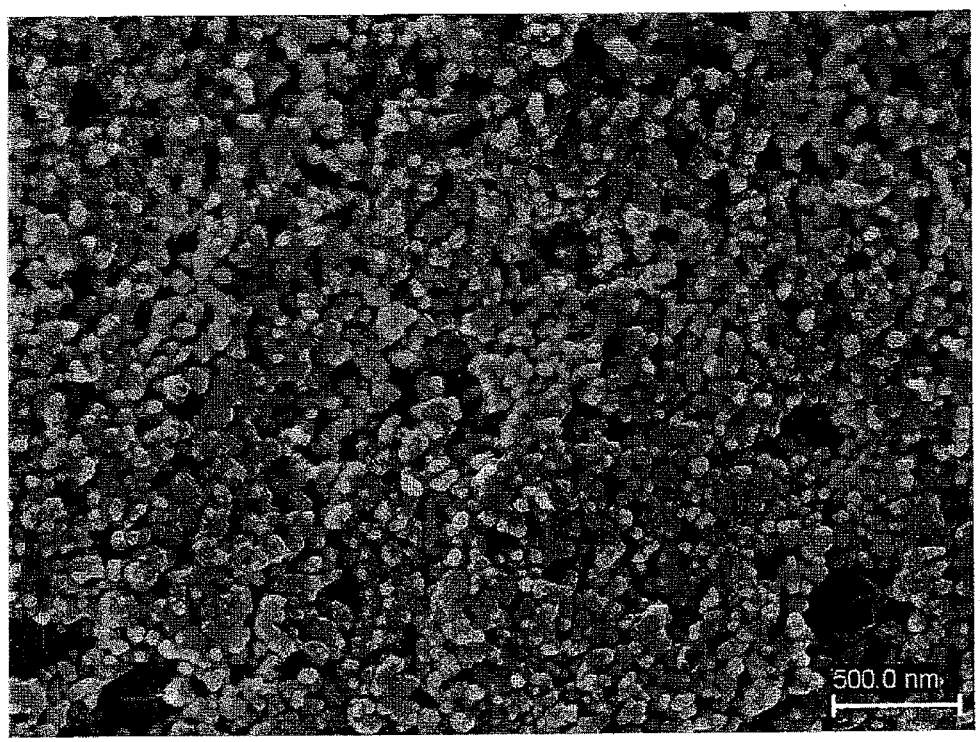
FIG. 8 shows an Ag nanoparticle film heated at 80° C. for 30 seconds.
Figure 9:
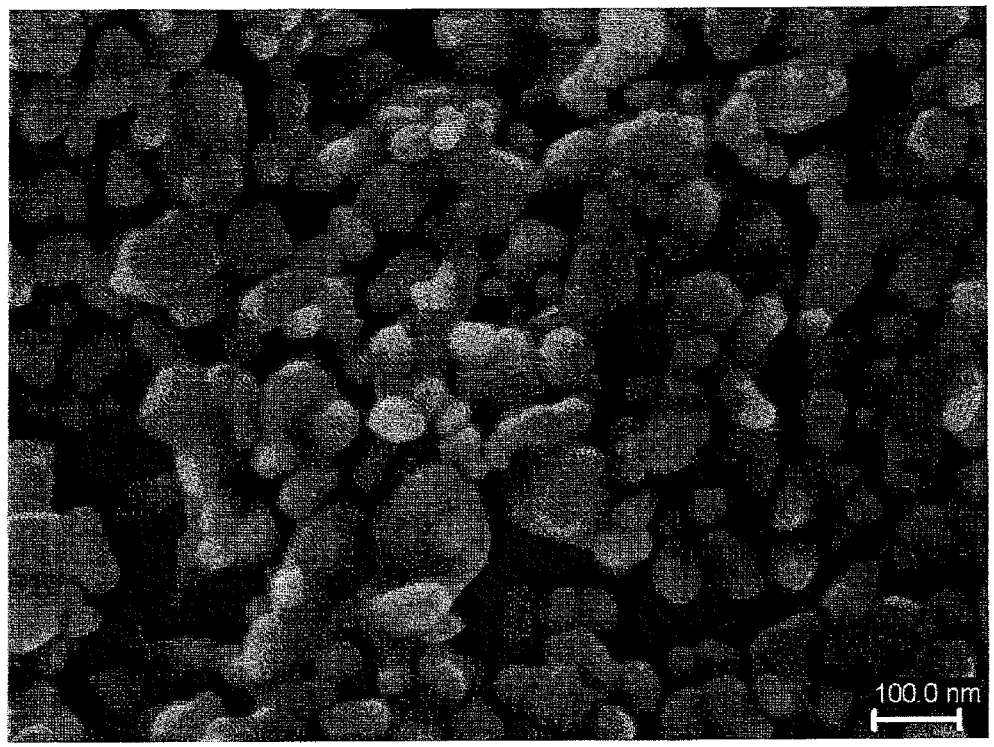
FIG. 9 shows the film from FIG. 8 at a closer magnification.
Figure 10:
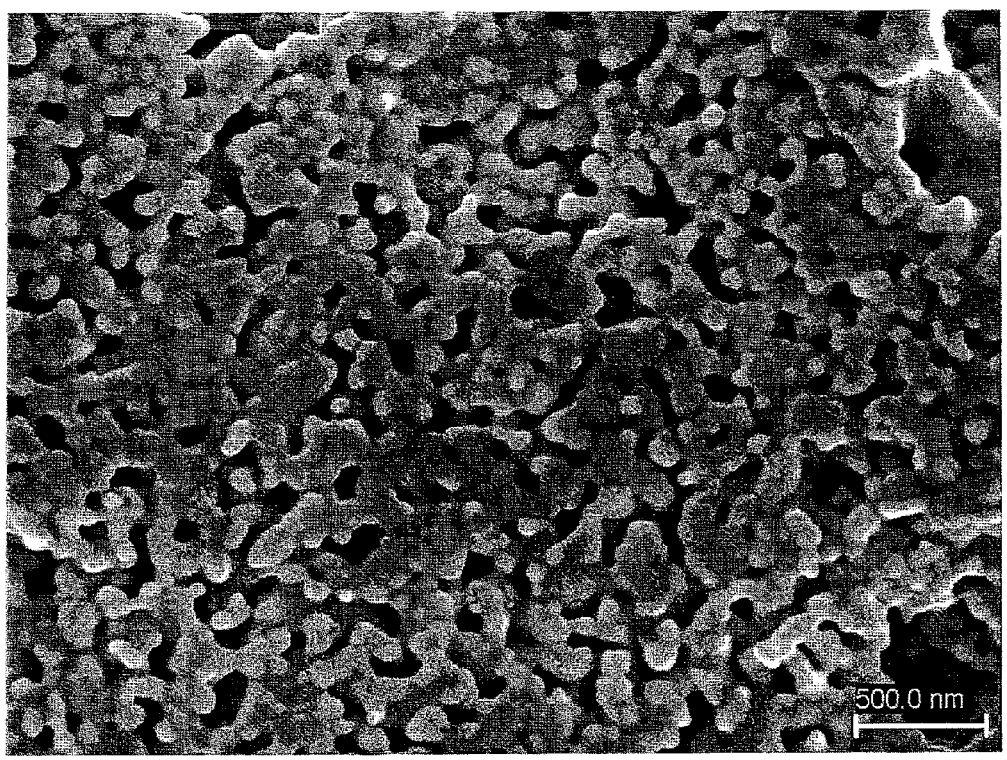
FIG. 10 shows an Ag nanoparticle film heated at 150° C. for 30 seconds.
Figure 11:
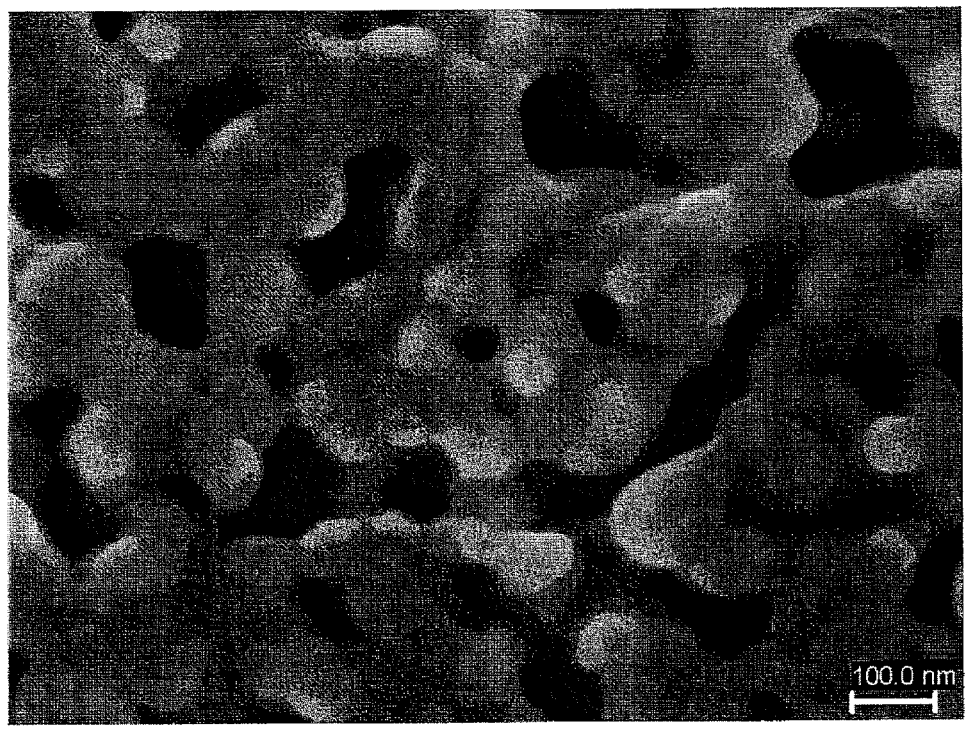
FIG. 11 shows the film from FIG. 10 at a closer magnification.

FIGS. 8-11 show the clustering of the nanoparticles that occurs during the heating processes. FIG. 8 shows an Ag nanoparticle film heated at 80° C. for 30 seconds, single nanoparticles can be formed and a lot of small clusters of nanoparticles. FIG. 9 shows the film from FIG. 8 at a closer magnification. FIG. 10 shows an Ag nanoparticle film heated at 150° for 30 seconds, as can be seen large networked clusters are formed. FIG. 11 shows the film from FIG. 10 at a closer magnification. The SERS amplification that is obtained using the SERS substrates shown in FIGS. 8 and 9 is between one and two magnitudes larger than that obtained using the SERS substrates shown in FIGS. 10 and 11.

Direct-current (dc) resistivity, or its converse, conductivity measures the ease of conduction of charge from one end of the sample to the other. Whereas, the SERS amplification depends on the local amplification of the high frequency electromagnetic field of the laser used as the excitation source in Raman scattering. Although the presence of free electrons is responsible for both the SERS effect and good dc conductivity, the two are not strongly correlated. In SERS spectroscopy a laser interrogates a small part of the sample while the dc conductivity is an average measurement of the whole sample over many conducting paths. Also, the physical mechanism which gives rise to SERS is totally different than what gives rise to high bulk conductivity. Therefore, although the dc conductivity can serve as a parameter indicative of the formation of clusters of nanoparticles, it is not strongly correlated to the SERS amplification. A better characterization of the efficacy of the heat treatment step can be achieved by monitoring the SERS amplification as a function of heating temperature and duration of heating, as described in the Example below. Such monitoring of SERS of oven-heated films can be used to determine the optimum temperature and duration of the heat treatment step for fabricating a particular SERS substrate.

For example, the heating process of the present invention should typically be terminated when an amplification of the Raman scattering signal of from about $1 \times 10^3$ to about $2.5 \times 10^{10}$, more preferably, from about $1 \times 10^6$ to about $1 \times 10^9$ and most preferably up to about $6 \times 10^8$, is achieved. Amplification is determined relative to the Raman scattering signal as measured using a normal Raman substrate which has not been provided with a Raman signal enhancing component, e.g. a glass slide without a coating can be used as a normal Raman substrate. Typically, the spacing between certain pairs of nanoparticles and/or nanoparticle clusters in the SERS substrate should be in the range of from about 0.1 to about 10 nm, more preferably from about 0.5 to about 8 nm and, most preferably, from about 1.0 nm to about 5.5 nm in order to create the desired hot spots. Also, the fractal distribution of the spacing between nanoparticles and/or nanoparticle clusters indicates that different spacing will be observed between different pairs of nanoparticles and/or nanoparticle clusters thereby allowing the SERS substrate to be used with a variety of different lasers. An example of the application of the process discussed above for formation of SERS substrates is given below.

Figure 12:
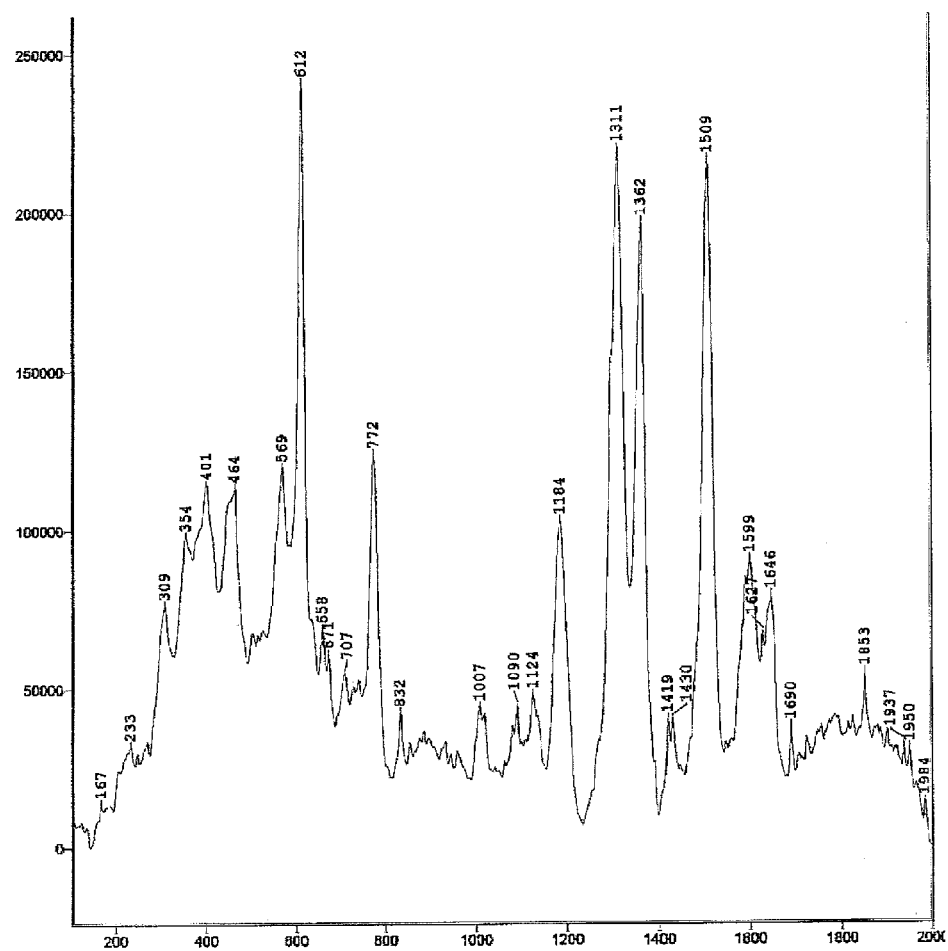
FIG. 12 is a graph showing the Raman spectrum of Rhodamine on a SERS substrate formed in accordance with an embodiment of the present invention using the heating process.

In one example, substrates 10, which had already been treated with nanoparticle ink 20, of approximately a size of 0.5 cm×2.0 cm were cut from four different pre-treated films. The sheets were heated at 175-200° C. for 30 minutes. This heat treatment evaporated the residual stabilizer 17 of polymer that is used in the fabrication of the film. It was found that a lower temperature of approximately 175° C. was adequate for this purpose. The heat treatment left a thin coating of silver oxide on the silver nanoparticles 18. This was removed by exposing the sheets to a 0.1 to 0.2 molar solution of acetic acid. The spectrum obtained using these completed SERS substrates is shown in FIG. 12, wherein the Raman spectrum of Rhodamine on a SERS substrate is shown.

Figure 13:
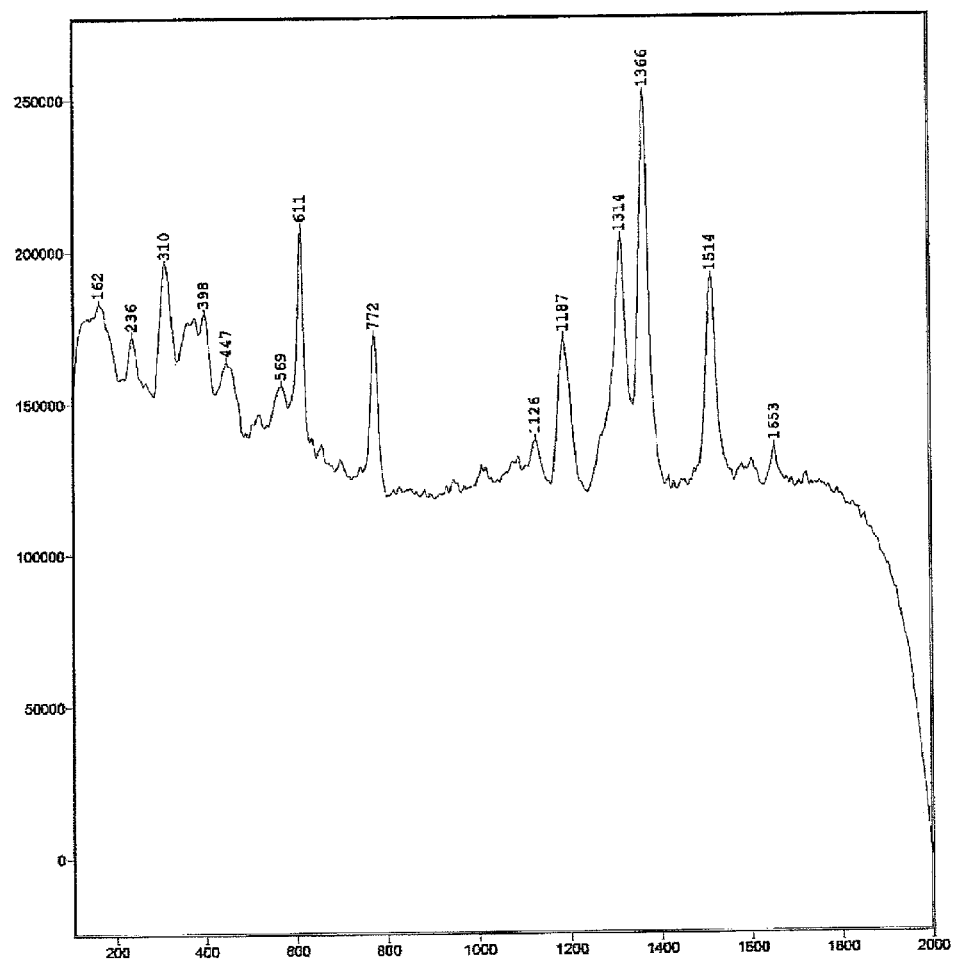
FIG. 13 is a graph showing the Raman spectrum of Rhodamine on a commercially formed SERS substrate.
Figure 14:
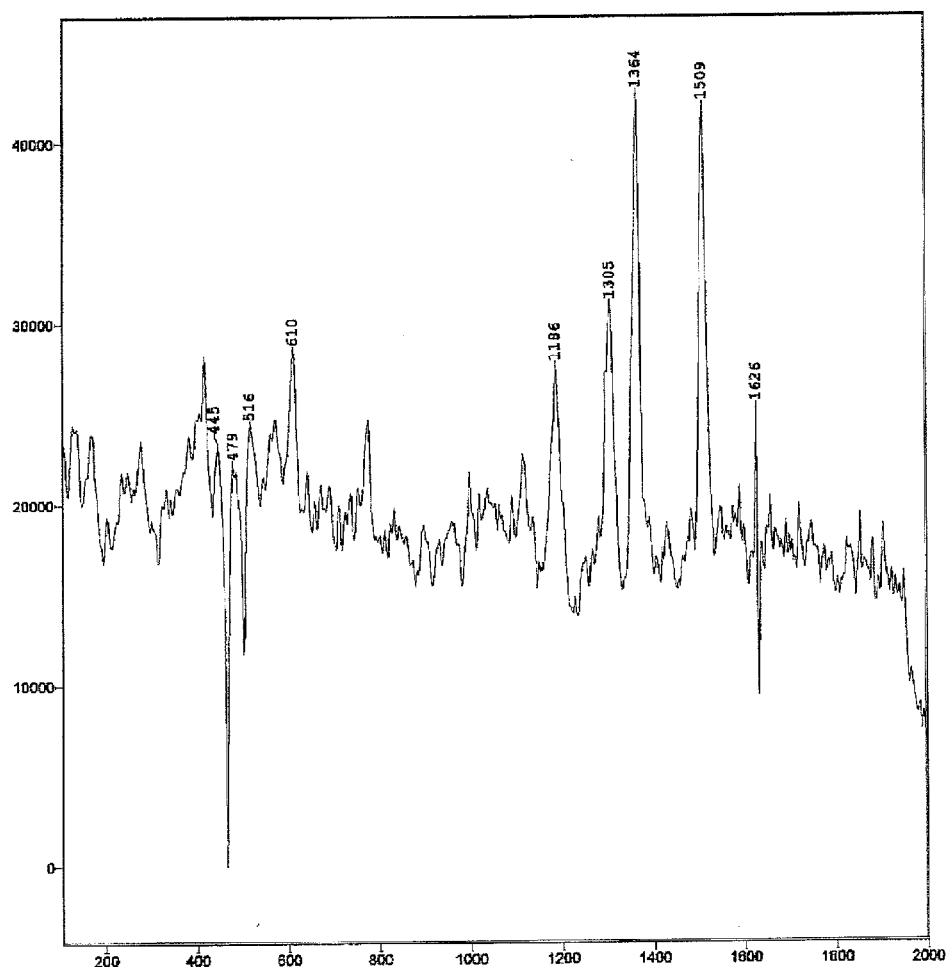
FIG. 14 is a graph showing the Raman spectrum of Rhodamine on a SERS substrate formed in accordance with an embodiment of the present invention using the nanoparticle ink.

FIG. 13 is a graph showing the Raman spectrum of Rhodamine on a commercially formed SERS substrate. FIG. 14 is a graph showing the Raman spectrum of Rhodamine on a SERS substrate formed in accordance with an embodiment of the present invention using the nanoparticle ink. By comparing the signal strength (i.e. amplification factor) of the fabricated SERS substrates with those obtained using commercially available SERS substrates illustrates that the signal strength of the SERS substrates made using the process of the present invention is stronger than that of the commercially available substrates. The commercially available substrates have an amplification factor of $10^6$. The spectral lines obtained by the SERS substrates fabricated in accordance with the process disclosed herein are approximately twice that in amplitude. The amplification factors are greater than $2 \times 10^6$.

In commercial production the colloidal silver particles are usually deposited on quartz/glass substrates using APTMS chemistry. This usually results in a monolayer of nanoparticles. When using an embodiment of the process of the present invention a substrate 10, made of quartz, is treated with a nanoparticle ink 20. Substrates 10 are then heated at 75° C. to evaporate the liquid vehicle. The resulting film is then heated at 175° C. for 10-30 minutes. This results in the nanoparticles moving into proximity with each other to produce "hot" spots for SERS amplification. In commercial production, hot spots may accidentally be created during the colloidal preparation. In the process disclosed herein these desirable hot-spots are preferentially created by controlling the thermal treatment.

In using the process of the present invention, very large SERS signal amplification can be achieved. This is accomplished because the analyte molecule can be located in the spacing 19 between two nanoparticles 18. This permits amplification of the intensity of the Raman scattering signal relative to the Raman scattering signal as measured prior to the heating step by a factor in the range of about $6 \times 10^6$ to about $2.5 \times 10^{10}$ when, for example, the separation between two silver nanoparticles 18 (i.e. a cluster 26) of diameter 90 nm is varied between 1.0 nm to about 5.5 nm. During the second heat treatment step, some nanoparticle pairs form favorable geometry by locating in close proximity with each other to thereby enable the enhanced amplification.

The present invention produces a SERS substrate that can provide enhanced amplification, when compared to commercially available SERS substrates. The process of the present invention controls the average distance between the nanoparticles by varying the time in which the nanoparticles are subjected to heat treatment. The process of the present invention also permits forming SERS substrates on a large scale while reducing the cost of producing the SERS substrates.

EXAMPLES

Example 1

Figure 15:
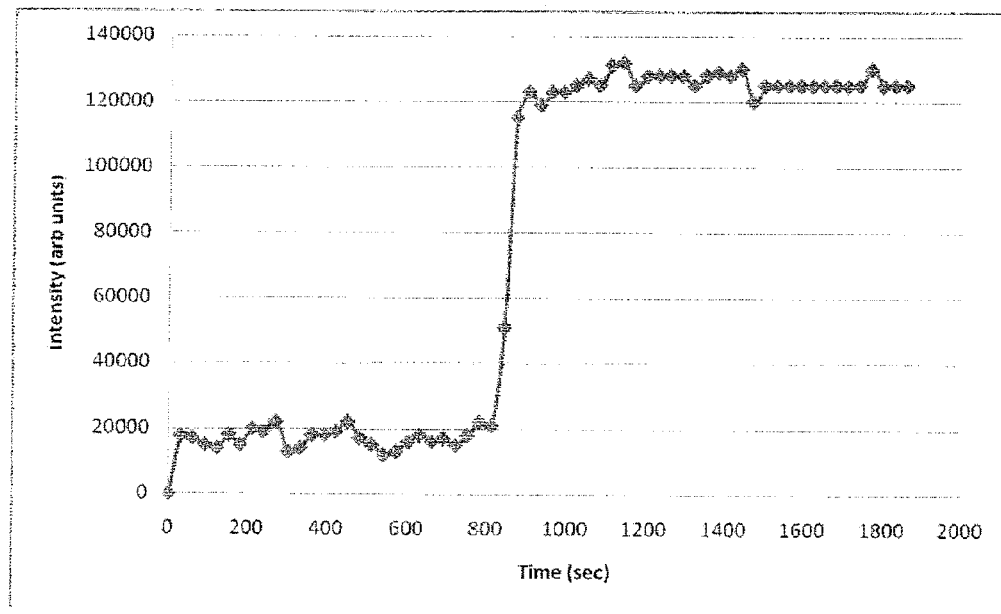
FIG. 15 shows the effect of laser heating and simultaneous monitoring of the 1364 cm$^{-1}$ Raman line in the SERS spectrum of Rhodamine6G.

FIG. 15 shows the effect of laser heating and simultaneous monitoring of the 1364 cm$^{-1}$ Raman line in the SERS spectrum of Rhodamine6G. A 10 microliter sample of 0.1 millimolar saline solution of Rhodamine6G was deposited on an air-dried but otherwise untreated Ag nanoparticle ink that had been previously deposited on a thin thermocouple. A 785 nm wavelength laser beam was focused to a spot 50 micron in diameter on the surface. The laser power was 25 mW. As can be seen from FIG. 15, the SERS signal remains barely above the noise level until the spot dries indicating removal of substantially all the liquid vehicle and the substrate temperature rises to about 100° C. and is maintained at that temperature for 60 seconds to thereby remove stabilizer from the nanoparticle ink. The baseline signal intensity of about 20,000 counts in FIG. 15 is the background signal due to fluorescence.

Example 2

Figure 16:
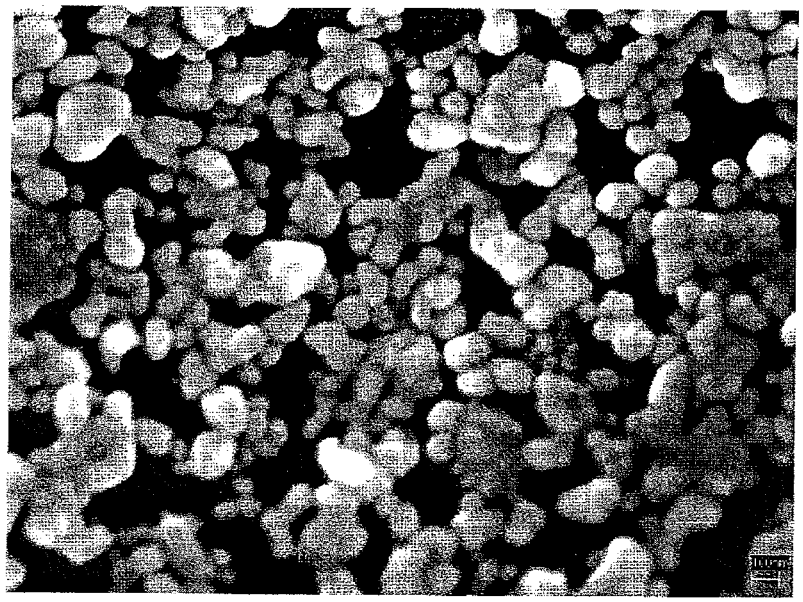
FIG. 16 is an SEM micrograph of an SERS substrate made in accordance with the present invention showing the fractal aggregate structure.
Figure 17:
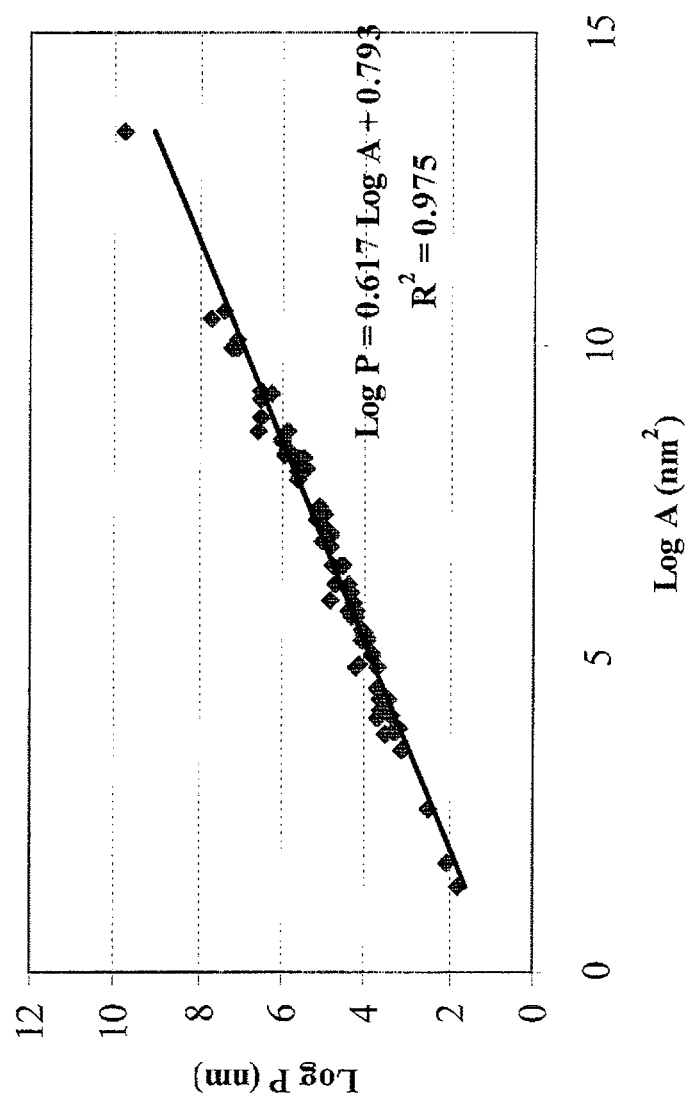
FIG. 17 shows the area to perimeter relationship for a silver colloid SERS substrate in accordance with the invention indicating a fractal aggregate.

One example of fractal structure produced in accordance with the method of the present invention is shown in the SEM micrograph of FIG. 16. From the log-log plot shown in FIG. 17 it can be seen that fractal aggregate having a fractal dimension of about 1.2 is obtained for this exemplary SERS substrate. To generate the plot of FIG. 17, least squares curve fitting is performed on the plots of the logarithm of the perimeter (P) versus the logarithm of the area (A) for the particles detected on the SEM image of FIG. 16. R2 values represent the excellent fit of the log P and log A values to the regression formula:

$$\text{Log } P = k + 2D/2 * \log A$$

where D represents the fractal dimension and k is a constant. The good linear fit of the curve of FIG. 17 confirms that a fractal aggregate was obtained.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method for fabricating surface-enhanced Raman scattering substrates including nanoparticles containing at least one material that enhances Raman scattering comprising the steps of:
    applying a nanoparticle ink to a surface of a substrate, wherein the nanoparticle ink comprises a liquid vehicle and a plurality of stabilized nanoparticles;
    heating the nanoparticle ink and the substrate in a first heating step to a first temperature for a first period of time to remove liquid vehicle; and
    heating the substrate and the plurality of stabilized nanoparticles in a second heating step at a second temperature higher than the first temperature for a second period of time to remove at least some of said stabilizer and form a nanoparticle layer on the substrate, wherein said second heating step is terminated when an amplification of the Raman scattering signal of from about $2 \times 10^6$ to about $2.5 \times 10^{10}$ is achieved.

2. The method of claim 1, wherein said second heating step is terminated when an amplification of the Raman scattering signal of from about $2 \times 10^6$ to about $1 \times 10^9$ is achieved.

3. The method of claim 1, wherein the first heating step removes substantially all of said liquid vehicle.

4. The method of claim 2, wherein the second heating step removes substantially all of said stabilizer.

5. The method of claim 1, wherein the first heating step is carried out at a temperature of about 50-100° C.

6. The method of claim 1, wherein the second heating step is carried out at a temperature of about 100-250° C.

7. The method of claim 1, wherein the nanoparticles comprise a material selected from the group consisting of silver, gold and copper.

8. A method for fabricating surface-enhanced Raman scattering substrates comprising the steps of:
    applying a nanoparticle ink to a surface of a substrate, wherein the nanoparticle ink comprises a liquid vehicle and a plurality of stabilized nanoparticles containing a material which enhances Raman scattering;
    heating the nanoparticle ink and the substrate for a sufficient time to remove liquid vehicle and at least some of said stabilizer and form a nanoparticle layer on the substrate, wherein said heating step is terminated when an amplification of the Raman scattering signal of from about $2 \times 10^6$ to about $2.5 \times 10^{10}$ is achieved.

9. The method of claim 8, wherein said heating step is terminated when an amplification of the Raman scattering signal of from about $2 \times 10^6$ to about $1 \times 10^9$ is achieved.

10. The method of claim 8, wherein the heating step removes substantially all of said liquid vehicle.

11. The method of claim 8, wherein the heating step removes substantially all of said stabilizer.

12. The method of claim 8, wherein the heating step is carried out at a temperature of about 50-250° C.

13. The method of claim 8, wherein the nanoparticles comprises a material selected from the group consisting of silver, gold and copper.

14. The method of claim 8, further comprising the step of placing the formed surface-enhanced Raman scattering substrate in a solution to remove at least some oxide from said surface-enhanced Raman scattering substrate after said heating step.

* * * * *

UNITED STATES PATENT AND TRADEMARK OFFICE
CERTIFICATE OF CORRECTION

PATENT NO. : 8,559,002 B2  Page 1 of 1
APPLICATION NO. : 12/933001
DATED : October 15, 2013
INVENTOR(S) : Tyagi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 230 days.

Signed and Sealed this

Fifteenth Day of September, 2015

Michelle K. Lee
*Director of the United States Patent and Trademark Office*